Figure 8:
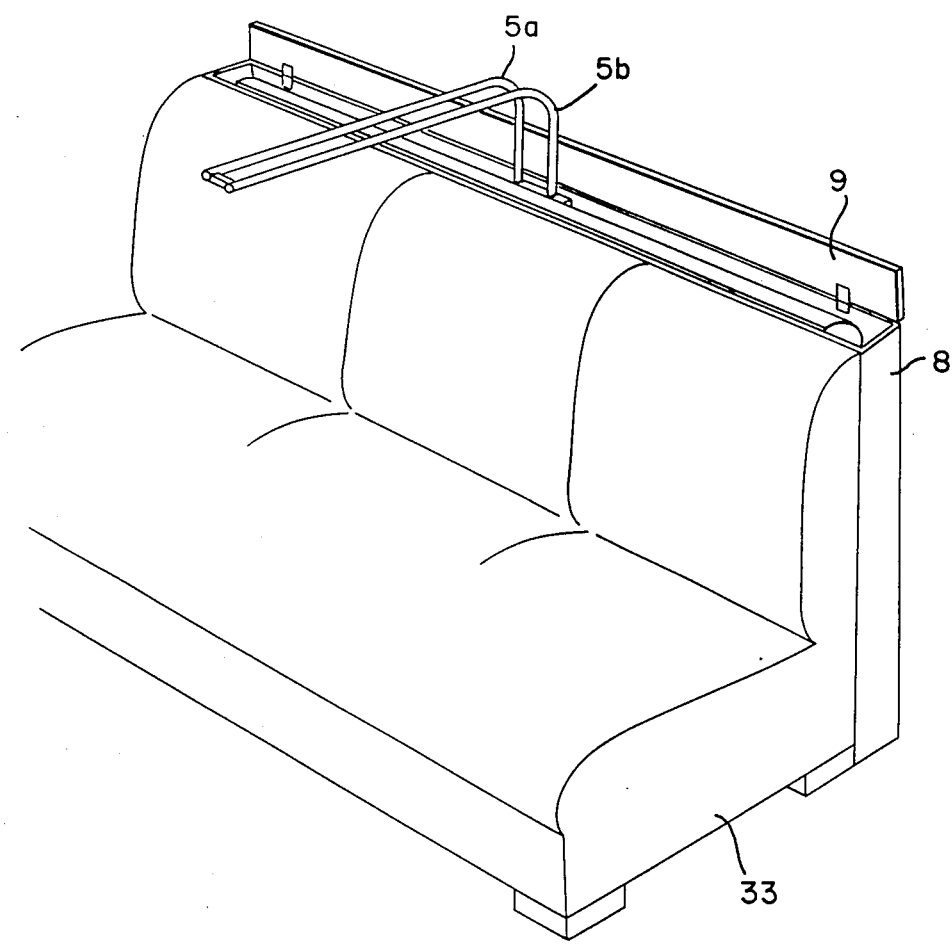

United States Patent [19]

Lindberg

[11] Patent Number: 4,744,016
[45] Date of Patent: May 10, 1988

[54] MEANS IN A SOLARIUM
[75] Inventor: Jan Lindberg, Ställdalen, Sweden
[73] Assignee: Extend Handelshus Aktiebolag, Orebro, Sweden
[21] Appl. No.: 33,105
[22] PCT Filed: Jun. 18, 1986
[86] PCT No.: PCT/SE86/00294
 § 371 Date: Feb. 27, 1987
 § 102(e) Date: Feb. 27, 1987
[87] PCT Pub. No.: WO87/00257
 PCT Pub. Date: Jan. 15, 1987
[30] Foreign Application Priority Data
 Jul. 1, 1985 [SE] Sweden .............................. 8503258
[51] Int. Cl.⁴ ............................................. F21V 21/14
[52] U.S. Cl. .................................... 362/131; 362/238; 362/250; 362/287; 362/413
[58] Field of Search ............... 362/127, 131, 239, 238, 362/250, 269, 287, 285, 413; 34/4, 243 C

[56] References Cited
U.S. PATENT DOCUMENTS
2,317,426 4/1943 Wilson ...................................... 34/4
4,265,029 5/1981 Jenkins .............................. 34/243 C Primary Examiner—Larry I. Schwartz
Attorney, Agent, or Firm—Dennison, Meserole, Pollack & Scheiner

[57] ABSTRACT

A solarium including a vertical guide-rail assembly having a casing-enclosed lower storage position and a selectively removable upper portion. A plurality of light-emitting units with cooperating reflectors mount perpendicularly across the guide-rail assembly and are displacable therealong and selectively received within the storage position.

9 Claims, 4 Drawing Sheets

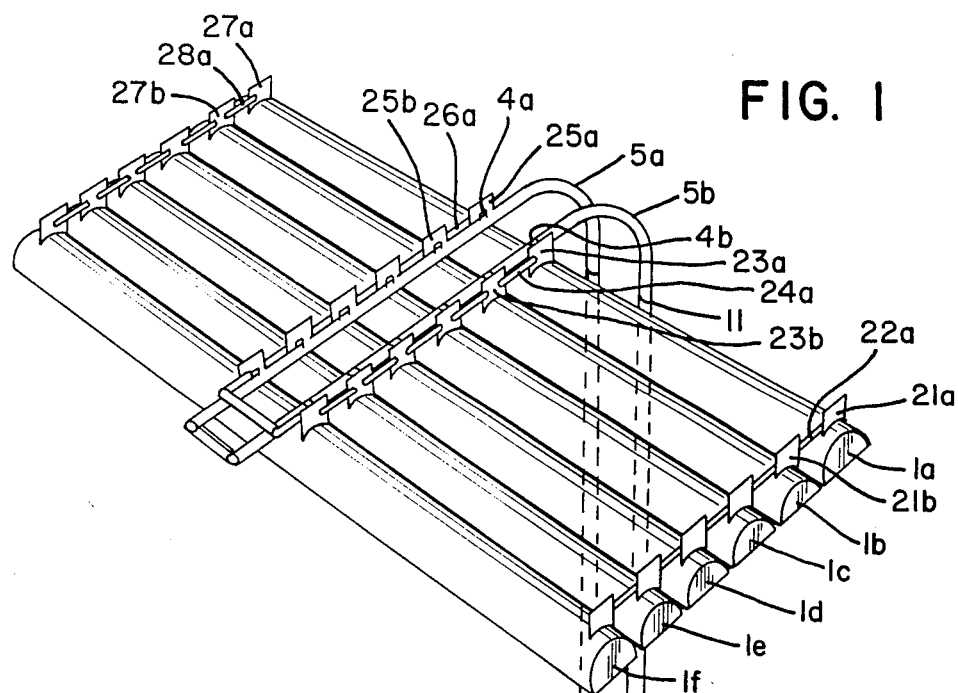
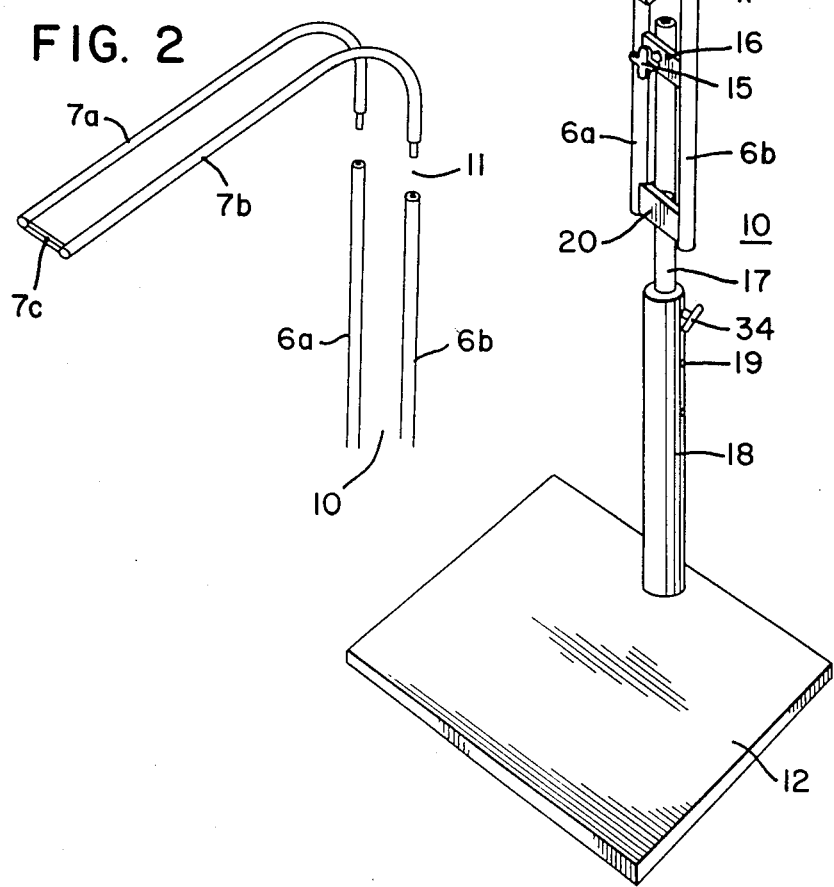

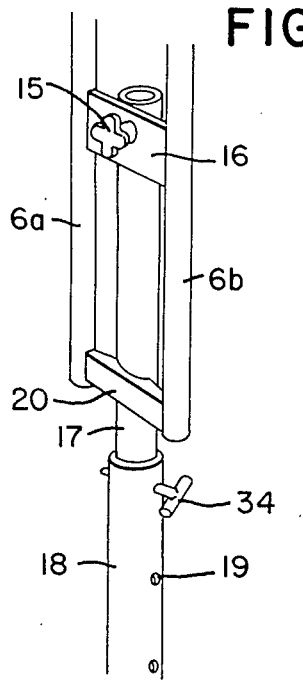
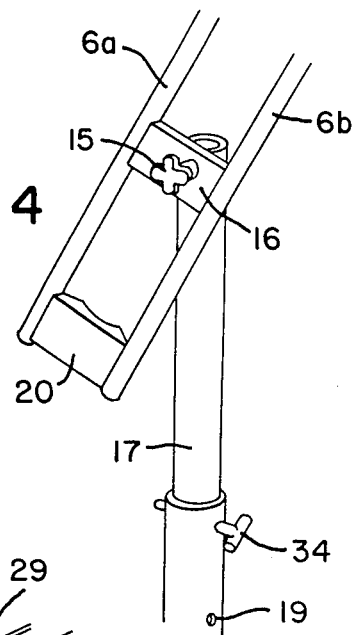
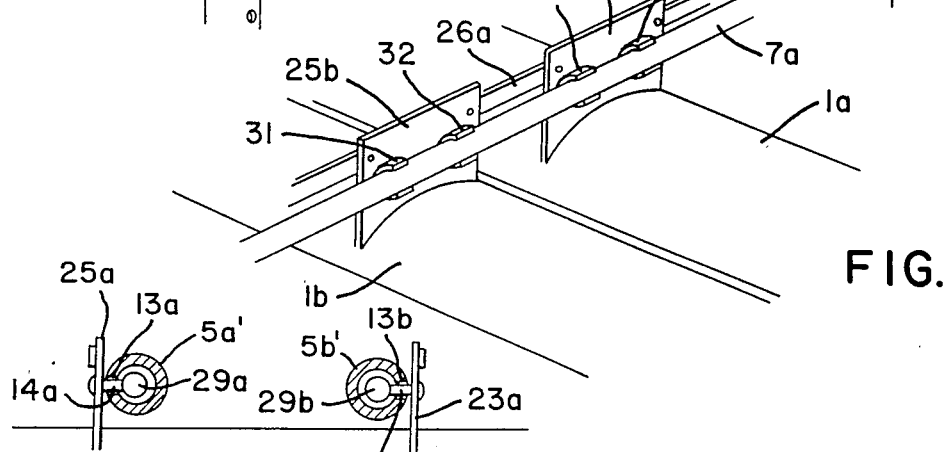
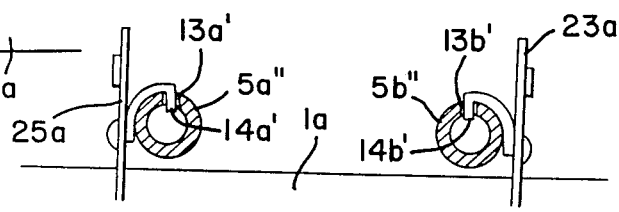
FIG. 3
FIG. 4
FIG. 5
FIG. 6
FIG. 7

MEANS IN A SOLARIUM

The use of a solarium has become extremely prevalent. They are available at public baths, gymnastic halls and health institutes. The desire has also arisen for a solarium at home. However, this is impractical if space is limited, since a solarium consists of a couch with a canopy above having substantially the same length as the couch and containing the sunray element and reflectors. A stand is provided enabling the canopy to be placed above a couch. A space is thus required equivalent to that taken up by a couch and its canopy.

The present invention aims at producing a solarium which facilitates housing it in a small space. This is achieved according to the present invention by utilizing a guide-rail assembly which can be shaped in various ways and transforms the canopy to the form of a roll-top consisting of a number of elongate elements joined together by links. Each element is provided with a member to cooperate with the guide-rail assembly. A solarium canopy in the form of a roll-top can therefore easily be moved along the guide-rail assembly.

According to an advantageous embodiment of the invention, a guide-rail assembly is secured to a flooring plate which is placed under a bedsettee, the guide rails extending vertically behind the back of the sofa from the flooring plate. At a certain distance from the flooring plate the guide rails curve over the sofa itself. The curved section is preferably removable from the vertical part. A solarium canopy in the form of a roll-top can now be moved along the guide rails from a vertical position behind the sofa to a horizontal position above the sofa. The back of the sofa generally corresponds in height to the breadth of the solarium canopy and when not in use, therefore, the roll-top canopy can be placed behind the sofa and the horizontal part of the guide-rail assembly can then be removed.

According to a preferred embodiment of the invention the vertical part of the guide-rail assembly, together with the roll-top solarium canopy, can be arranged in a closable box behind the sofa. Such a box need be no higher than 20 cm.

Additional features of the present invention are revealed in the accompanying claims.

Figure 9:
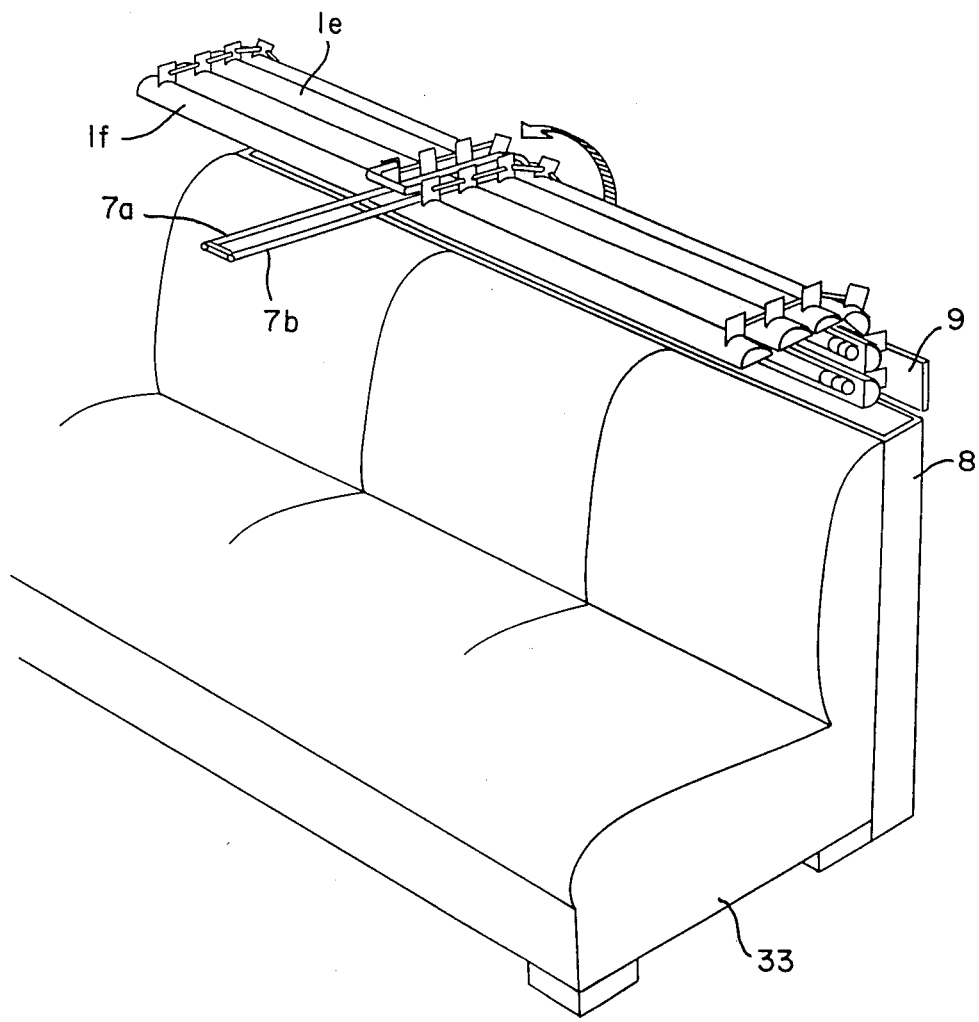

The present invention will be described in more detail with reference to the accompanying drawings in which FIG. 1 shows a complete solarium according to the present invention, FIG. 2 the upper portion of a guide-rail assembly for the part of the solarium containing the light-emitting units, FIGS. 3–4 show the lower part of the guide-rail assembly in two different positions, FIGS. 5–7 show three alternative versions of members cooperating with the guide-rail assembly, and FIGS. 8–9 show cooperation of the solarium with a sofa in two different stages.

FIG. 1 shows a solarium canopy comprising six elongate units 1a, 1b, 1c, 1d, 1e and 1f, each elongate unit including a reflector and light-emitting units either in the form of screw-in bulbs or strip-lighting. Each unit is provided at each end with an outwardly directed flange. On the unit 1a these flanges are designated 21a and 27a. One end of the flange 21a is flexibly connected to a link 22a, the other end of which is flexibly connected to the flange 21b of the next unit 1b. Flange 27b of unit 1b is flexibly connected to one end of a link 28a, the other end of which is flexibly connected to the flange 27a belonging to unit 1a. The remaining units are connected in the same way, giving the six connected units the nature of a roll-top, each unit being movable about an axis parallel to the longitudinal axis of the unit. Each unit (1a) is provided centrally with two flanges (24a and 25a). Two rows of flanges are thus formed down the middle of the six units, these flanges being linked together in the same way as the flanges at each end of the units. Flanges 25a and 25b are thus connected by a link 26a. Each flange (24a and 25a) are provided on opposing sides with clawlike members 4a and 4b designed to cooperate with a guide-rail assembly consisting of two parallel rods 5a and 5b. The clawlike members 4a and 4b grip the rods so that each unit (1a) is displaceable along the rods 5a and 5b. The two rods 5a and 5b are provided with a vertical section 6a and 6b and a substantially horizontal section 7a and 7b. These two parts can be separated from each other as shown in FIG. 2. The rod sections 7a and 7b are joined by a connecting unit 7c at the lefthand end in the figure. The two rods 6a and 6b are joined at the lower end 10 by a connecting unit 20 and by a second connecting unit 16 above the first unit 20. The connecting unit 16 is pivotably attached to a rod 17 by means of a screw 15. The two rods 6a and 6b can be pivoted to the desired position with the aid of the screw 15, and secured there. The rod 17 is vertically movable in a sleeve 18 provided with a number of holes 19 cooperation with corresponding holes in the rod 17. The vertical position of the rod 17 is adjusted by means of a cotter 34 inserted in one of the holes 19 and a hole, not shown, in the rod 17. The sleeve 18 is firmly secured to a flooring plate 12.

FIG. 5 shows in more detail the design of the clawlike members. Each flange 25a has two clawlike members 29 and 30 which may be of plastic or some other suitable material allowing displacement of the members 29 and 30 along the rod 7a without leaving the rod.

FIG. 6 shows that the clawlike members 29 and 30 may be replaced by a pin 14a protruding into a groove 13a in the rod 5a'. The groove 13a extends along the entire length of the rod 5a'. The rod 5a' is hollow like a pipe and the pin 14a is provided with an enlarged portion 29a preventing it from leaving the groove 13a.

FIG. 7 shows a third version of the pin and groove. The rod 5a" is in the form of a pipe and its groove 13a is directed so that its axis is parallel to cooperating flanges included in the row of flanges which also includes flange 25a. A pin 14a' protrudes from each flange, shaped so that only its tip protrudes into the groove 13a', the rest of the pin following th outer contour of the rod.

The solarium according to the present invention is utilized as follows: When not in use the units 1a to 1f are moved along the guide-rail assembly 5a and 5b to be linked only to the part of the guide-rail assembly including the rod sections 6a and 6b. Sections 7a and 7b are removed and in this state the solarium can easily be placed behind a cupboard or sofa 33. It thus takes up a minimum of space. The solarium may in this state be enclosed in a casing in the form of a box 8 with a lid 9, as shown in FIG. 8. When the solarium is in use the person to receive sun-ray treatment can use the sofa to lie on. When the solarium is to be used, the lid 9 is opened and the upper part of the guide-rail assembly, the rods 7a and 7b, are fitted to the vertical part consisting of rods 6a and 6b. These rods are provided at their upper ends 11 with holes into which protrusions in the upper guide-rail assembly can be inserted. FIG. 8 shows the two guide-rail sections joined together. All that is necessary to complete the solarium is for the units 1a to 1f to be pulled up from the box 8 each unit sliding along the rods 5a and 5b. FIG. 9 shows the units 1a to 1f on their way towards the operating position as shown in FIG. 1. Here the units 1a to 1f are parallel to the couch below where the person is to receive sun-ray treatment. The units 1a to 1f can be adjusted to the desired distance from the couch with the aid of the holes 19 and cotter 34. The screw 15 allows the units 1a to 1f to be adjusted to the desired angle in relation to the couch surface.

From the above it will be seen that a solarium has been created which can be substantially hidden behind the back of a sofa when not in use. When it is to be used, it is only a question of fitting on the horizontal part of the guide-rail assembly and pulling up the roll-top light elements from their place behind the sofa. A sofa used for this purpose would probably only have to be drawn out some 20 cm from the wall to accommodate the thickness of the sun-ray equipment.

I claim:

1. In a solarium comprising a canopy containing light-emitting units and a holder for said canopy, said canopy comprising a number of rigid elongate bodies located side by side and parallel to each, said bodies being articulated with respect to each other with each body being pivotable about an axis parallel to the longitudinal direction of the body, each body including, along the length thereof, at least one of said light-emitting units with cooperating reflector means, said holder comprising a guide-rail assembly and mounting means on each body cooperating with said guide-rail assembly, said bodies being displaceable along the guide-rail assembly substantially perpendicular thereto, said guide-rail assembly including a section forming a storage position for selectively receiving said bodies, the guide-rail assembly including a portion extending beyond said storage position, said portion being selectively removable from the section forming the storage position.

2. A solarium according to claim 1 wherein the section of the guide-rail assembly forming the storage position is arranged vertically.

3. A solarium according to claim 2 including a casing enclosing said vertically arranged guide-rail section, said casing being configured to receive and surround said elongate bodies in the storage position.

4. A solarium according to claim 3 including a flooring plate mounting said section.

5. A solarium according to claim 4 wherein said guide-rail assembly comprises two spaced parallel rails, said mounting means comprising two members, each cooperating with one of said rails.

6. A solarium according to claim 5 wherein each member is mounted on the corresponding rail for sliding adjustment of the corresponding body therealong.

7. A solarium according to claim 6 wherein each guide-rail includes a groove longitudinally therealong, each member including a protruding element slidably received in the groove of the corresponding rail.

8. A solarium according to claim 6 including means mounting the guide-rail assembly for pivotable adjustment about a vertical axis.

9. A solarium according to claim 8 including means mounting the guide-rail assembly for vertical adjustment.

* * * * *